United States Patent
Lunati et al.

(10) Patent No.: US 9,234,477 B2
(45) Date of Patent: Jan. 12, 2016

(54) METHOD FOR OPTIMIZING THE OPERATION OF A THERMAL ENGINE BY DETERMINING THE PROPORTION OF OXYGENATED COMPOUNDS IN THE FUEL

(75) Inventors: Alain Lunati, Aix en Provence (FR); Johan Fournel, Aix en Provence (FR)

(73) Assignee: SP3H, Aix-en-Provence (FR)

(*) Notice: Subject to any disclaimer, the term of this patent is extended or adjusted under 35 U.S.C. 154(b) by 1282 days.

(21) Appl. No.: 12/989,308

(22) PCT Filed: Apr. 21, 2009

(86) PCT No.: PCT/FR2009/000476
§ 371 (c)(1),
(2), (4) Date: Aug. 26, 2011

(87) PCT Pub. No.: WO2009/138585
PCT Pub. Date: Nov. 19, 2009

(65) Prior Publication Data
US 2012/0226425 A1 Sep. 6, 2012

(30) Foreign Application Priority Data
Apr. 24, 2008 (FR) ..................... 08 02314

(51) Int. Cl.
G06F 19/00 (2011.01)
F02D 41/24 (2006.01)
F02D 19/06 (2006.01)
(Continued)

(52) U.S. Cl.
CPC ........ *F02D 41/2422* (2013.01); *F02D 19/0628* (2013.01); *F02D 19/084* (2013.01); *F02D 19/087* (2013.01); *F02D 41/0025* (2013.01); *F02M 25/0227* (2013.01); *F02M 25/0228* (2013.01); *G01N 21/359* (2013.01); *G01N 21/3577* (2013.01); *F02D 19/0623* (2013.01); *F02D 2200/0611* (2013.01); *Y02T 10/36* (2013.01)

(58) Field of Classification Search
CPC ............ G01N 21/359; G01N 21/3577; G01N 33/2829; F02D 41/2422; F02D 19/087; F02D 2200/0611
USPC ................ 701/102, 101; 356/133; 73/114.52; 250/339.12
See application file for complete search history.

(56) References Cited

U.S. PATENT DOCUMENTS 5,121,986 A * 6/1992 Rutz .............................. 356/133
5,362,965 A * 11/1994 Maggard .................. 250/339.12
(Continued)

FOREIGN PATENT DOCUMENTS

FR 2 542 092 9/1984
FR 2 888 323 A1 1/2007
(Continued)

*Primary Examiner* — Mahmoud Gimie
*Assistant Examiner* — David Hamaoui
(74) *Attorney, Agent, or Firm* — Arent Fox LLP

(57) ABSTRACT

The invention relates to a method for optimizing the operation of a thermal engine having combustion parameters controlled by an electronic housing and at least one engine mapping, characterized in that the method comprises: a step of carrying out a near-infrared spectroscopic analysis of a bio-fuel containing a mixture of alcohols and/or ethers and/or water in order to determine the proportions of water and of at least one other oxygenated compound of the alcohol and/or ether type contained in the bio-fuel; and a step of selecting and/or modifying said mapping on the basis of the analysis result in order to optimize the operation of the thermal engine.

7 Claims, 13 Drawing Sheets

(51) Int. Cl.
*F02D 41/00* (2006.01)
*F02M 25/022* (2006.01)
*G01N 21/359* (2014.01)
*F02D 19/08* (2006.01)
*G01N 21/3577* (2014.01)

(56) References Cited

U.S. PATENT DOCUMENTS 6,612,269 B2 * 9/2003 Heffel et al. .................. 123/1 A
6,690,015 B1   2/2004 Benes et al.
7,676,316 B2 * 3/2010 Lunati et al. .................. 701/103
8,148,692 B2 * 4/2012 Lunati et al. .................. 250/343
8,457,863 B2 * 6/2013 Fournel et al. ................ 701/103

FOREIGN PATENT DOCUMENTS

| | | |
|---|---|---|
| FR | 2 904 951 A1 | 2/2008 |
| WO | WO 94/08226 A1 | 4/1994 |
| WO | WO 2006/100377 A1 | 9/2006 |
| WO | WO 2006/101653 A2 | 9/2006 |
| WO | WO 2006100377 A1 * | 9/2006 |
| WO | WO 2008/004387 A1 | 1/2008 |

* cited by examiner

METHOD FOR OPTIMIZING THE OPERATION OF A THERMAL ENGINE BY DETERMINING THE PROPORTION OF OXYGENATED COMPOUNDS IN THE FUEL

CROSS-REFERENCED TO RELATED APPLICATION

This application is a National Stage entry of International Application No. PCT/FR2009/000476, filed Apr. 21, 2009, which claims priority to French Application No. 0802314, filed Apr. 24, 2008, the disclosure of the prior application is incorporated in its entirety by reference.

TECHNICAL FIELD OF THE INVENTION

The invention relates to a method for optimising the operation of a thermal engine.

The invention more particularly relates to engines supplied with bio-fuels.

STATE OF THE ART

Thermal internal combustion engines must meet always stricter requirements as regards $CO_2$, $NO_x$, HC emission standards and this is the reason why the proportion of bio-fuels in the commercial fuels, i.e. gasoline and gas-oil, such as bio-ethanol and bio-diesel which are manufactured from multiple sources enabling the substitution of oxygen atoms for carbon atoms has been rising for a few decades.

The new supply networks use renewable resources from agriculture such as canola seeds, maize, sunflower, sugar-cane, soya, cellulose and algae, to mention only a few.

Then, the reflections led for several decades tend to take into account the total emissions, i.e. "from the well to the wheel", which thus include not only the impact of the engine and of the combustion, but the global impact of the fuel, from the extraction to the production thereof and the transportation thereof, too. This is the reason why, even though, in terms of consumption, a vehicle having a positive ignition engine complying with the Euro IV Standards uses a mixture by volume composed of 85% of ethanol and 15% of gasoline (E85), it uses between 30 and 40% more fuel than when it uses gasoline without ethanol, but the gain in $CO_2$ emission at the exhaust passage is reduced by 6% on an average and more particularly by 38% if the whole "from the well to the wheel" cycle is taken into account.

The "clean" aspects of such fuels more and more integrate the notions of renewable energy and sustainable development and the impact on the water and basic food resources supplies for the poorer populations.

According to the rules prevailing since the 80s, such bio-fuels are introduced into the traditional fuels in various proportions. The present trend and the plans considered by the governments favour the significant increase in the respective proportions of bio-fuels in the fuels resulting from the refining of crude oil. This is the reason why American reformulated gasoline has 10% of bio-ethanol or E10 and why E26 (percentage of ethanol=26%) or E100 (percentage of ethanol>93%) can be found in Brazil or E85 in Europe.

Similarly, the integration of bio-diesel in gas-oil is on an average 4% (B4) in Europe and the target is the authorisation of selling B10, then B30, and potentially B100. As for Europe, it has favoured the integration of more or less significant quantities of molecules of the ether type, more precisely MTBE, ETBE or TAME, since 1985. However, in Europe, fuels of the E85 type are now sold in service stations.

Many studies carried out since 2002 have also studied the possibility of introducing alcohols such as ethanol into diesel and are studying the impacts on combustion, consumption and polluting emissions.

However, the increase in the bio-fuel content in gasoline and gas-oil is not without risk and it is limited by the necessity of providing specific engine adjustments and arrangements of engine technologies adapted to high contents in bio-fuels, failing which the combustion will be degraded as well as the engine and polluting emissions and $CO_2$ emissions will be generated which will be more important than with conventional fuel.

A second risk is directly connected with the hydrophilic characteristic of alcohols and their capacity of storing and keeping water, more particularly within the scope of an unintentional pollution of the distribution network, during storage operations or for more mercenary reasons, by voluntary additions of water even of a few percents by volume.

In addition, the method of production of ethanol is based on an extractive distillation method and results in a known azeotrope including 95% of ethanol and 5% of water. Without any other separating method, it is not possible, thus, to obtain a yield of alcohol of more than 95% of ethanol and 5% of water.

The water contained in the bio-fuel causes the quicker oxidization and corrosion of the mechanical elements of the fuel circuit, the tank, the pumps as well as the injection system. The combustion is also affected as is the result of the oxygen sensor which is distorted. This sensor system is however required within the scope of the OBD diagnostic and enables the closed loop regulation of the air/fuel ratio about the value 1, so as to optimise the operation of the three-way post-treatment catalyst and the regulation of the CO, HC and $NO_x$ emissions of positive ignition engines.

Today, in order to optimise the operation of a thermal engine supplied with such fuels, the solutions considered and selected are based on approaches and physical sensors of the conductance and conductivity type or an approach without any sensor which is also called a soft-sensor based on a more or less rapid learning cycle of the oxygen content of the air-fuel mixture from the results provided by the oxygen sensor.

However, all the technologies presented so far do not make it possible to distinguish the origin of the oxygen contained in the air-fuel mixture. As water is present, this entails extremely varying mistakes in the prediction of the percentage of ethanol and the percentage of oxygen from the physical measuring sensors of the conductance type or non convergence in the learning loop, in the case of soft-sensors. The impact of the error in the measurement of the percentage of bio-fuel can even be higher according to the alkalinity of water and the quantity of dissolved salts.

The informations and conclusions mentioned in the document by B. HAUET—SIA Mar. 13, 2007 clearly explain the problems relating to the specific adjustments of the controlled ignition engines when a mixture containing bio-ethanol is used and impacts on the combustion, starting of the engine and polluting emission strategies, as a function of an external parameter such as temperature and thus the necessity of knowing accurately the data relating to the bio-fuel.

The work carried out by Dr. CHANDRA in 1998 for the Canadian government (direction of transport systems—general directorate of prevention of pollution in the environment of Canada) show the effects of volatility of bio-fuels on the engine efficiency during the phases of start-up in hot weather and in cold weather, as well as the impacts of the weakening of the air/fuel ratio more particularly in an open loop and of the jogging phenomenon which can also be detected when accelerating with a heavy load or a full load of the engine and which significantly deteriorates the driveability of the vehicle. The impact on the management of the engine knock limit has been discussed with an effect which is different from the gain in octane of the basic gasoline by adding bio-fuel which very significantly affects the sensitivity of fuel (RON-MON difference) and thus makes it necessary to revise the strategies of the engine knock control.

Then there exists a need for precisely determining the quality and the quantity of the composition of the bio-fuel and more particularly the composition in oxygenated compounds.

The quantity and numerous documents and articles which have offered for 25 years solutions relating to the determination of the oxygen contents in the fuels show the necessity and the importance of the measurement for optimising the strategies relating to the starting, combustion and post-treatment of engines also called flex fuel.

Thus, document U.S. Pat. No. 7,163,002 deals with a method for adjusting the quantity of fuel injected for the cold operation of an engine as a function of the volatility of the fuel.

Document U.S. Pat. No. 5,893,349 provides to use a learning loop and a step-by-step retro-control method from the air/fuel mixture calibration tables for the cold engine start.

The document U.S. Pat. No. 5,492,101 provides for the adjustment of the parameters of an engine from a plurality of sensors which make it possible to determine the properties of the fuel in order to adjust the engine injection parameters.

But none of the sensors is described in detail and no mention is made either of the constraints relating to the presence of an alcohol based bio-fuel and the interactions with water and temperature.

Documents US2003/00201494, US2004/0004487 and US2005/0253599 provide for an indirect determination of the oxygen content and the percentage of ethanol from a fuel sensor using the principle of variation in the measurement of the conductance/capacitance of a mixture containing bio-fuel and the correlation between the inductance current measured between the electrodes of the sensor and the percentage of oxygen.

Document USD2004/0253599 describes a similar principle which is a method for determining the oxygen content of a fuel/ethanol mixture from the measurement of temperature and impedance of the mixture.

Other approaches have also been provided, more particularly in document US2005/0247299 based on a sound wave sensor making it possible to determine the density and viscosity of a fuel, and document EP0461156 which provides for the adjustment of the air/fuel ratio of an internal combustion engine from the measurement in the combustion chamber of the ionisation signal which can be correlated with the properties of the fuel and more particularly the oxygen content and thus the ethanol content thereof.

The document U.S. Pat. No. 5,435,285 provides for the utilisation of an optical sensor based on the measurement of the fuel refraction index and the angle variation between a fuel containing ethanol and a fuel containing no ethanol.

Now, none of the above-mentioned documents, the methods or systems of which have already been implemented, never describe the effects of alcohol-water or alcohol-water-esters mixtures and the effect thereof on the measurement of the oxygen content and by correlation the alcohol content of a fuel-bio-fuel mixture, as well as the impact on the variation in the number of carbon atoms in the carbonated alkyl radical associated with the O—H bond.

However, as from 1983, ITO and al. in document U.S. Pat. No. 4,391,253 favours the limitation of the conductivity/inductance type sensor in the determination and prediction of the oxygen content of an alcohol-fuel mixture, more particularly because of the presence of impurity such as water which randomly and significantly affect the transformation of the current from the sensor into a correct and accurate value of the ethanol content. However, no method since then has been capable of providing a reliable solution to this problem.

In addition, such documents do not provide either for the utilisation of a spectrometric type sensor making it possible to measure the interactions between light and material more particularly in the infrared or near-infrared zone.

Document FR2542092 describes the utilisation of a near-infrared sensor within the 700 nm-1,700 nm area for determining the alcohol content of an alcohol-fuel mixture. The document provides the possibility of using two measuring cells, one being filled with the reference alcohol, methanol and the other with the bio-fuel to be measured, more particularly within the 900-1,000 nm and 1,450-1,600 nm areas.

However, this document as well as those by Maggard et al. do not describe nor provide solutions to correct the well-known effects of temperature on the distortions of the measurement of absorbance at the selected wavelengths for an hydrocarbon-alcohol mixture, and more particularly do not take into consideration the spectral corrections and the interactions which more particularly affect an ethanol-fuel or methanol-fuel mixture in presence of water.

Now, the hydrophilic characteristic of alcohol cannot be neglected in the case of bio-fuels and thus limits the scope and the possibility of application of the documents in a laboratory and make them inapplicable in the scope of an application aboard and automated systems.

As a matter of fact, the inventors have neglected the known effects of drift in the wavelengths characteristic of the O—H bond with respect to the theory on the first, second and third harmonics due to FERMI resonances resulting from the interaction of a fundamental vibration with an harmonic band or a combination band which have approximately the same wavelength, and which belong to the same symmetry group or DARLING DENNISON group resulting from the interactions between equivalent energies vibrations in the case of the water molecule or CORIOLIS interactions.

The journal of NIR spectroscopy vol. 10 no 1 or ANALUSIS MAGAZINE, 26 no 4, 1998 gives a rather precise description of the drifts in the various wavelengths of the vibration values of the O—H bond in the regions of the first, second and third harmonics and the combination region, more particularly for the water-methanol, water-ethanol or water-propanol mixtures with variations by 0% to 100%. At 25° C., the displacement of the characteristic wavelength with respect to the theoretical values depends on the alkyl radical associated with the O—H bond, because of the known phenomenon of displacement of the electronic doublet of oxygen on the $CH_3$ and $CH_2$ groups. The discrepancies with respect to the expected band can reach 5 nm and even more in the case of an increase in temperature.

In addition, the current systems such as described or used cannot prevent the more or less uncontrolled phenomena of demixing in the fuel/bio-fuel mixture in the case of an alcohol-water mixture in fuels, as a function of the outside temperature resulting in the appearance of 2 phases in the tank and in significant effects in the driveability of the vehicle (such as a smooth operation, stalling, pollution) and the optimisation of the combustion phase.

The integration of bio-fuel of the alcohol type as a base in conventional fuels also favours the appearance of non-linear phenomena which are very penalising for the volatility of mixtures between 5% and 20% of alcohol (E5 and E20) as well as in the distillation values of the first 50% of the mixture. The range of the non-linear phenomena also depends on the type of the bio-fuel used and is all the more important since the alkyl radical related to the alcohol group is small (methanol has more effect than ethanol, then propanol and butanol). Such non-linear phenomena may result in the appearance or non-appearance of vapour locks and have a real effect on the phases of cold engine start or warm engine start. In addition, none of the sensors described or of the solutions is functional in the case of auto-ignited thermal engines of the diesel type.

Thus, one of the limits today in the increase in the integration of bio-fuels in conventional fuels thus results from the impossibility of the existing solutions to rigidly and accurately measure in every case the oxygenated compound contents and more particularly the capacity of detecting the presence of water in the bio-fuel and thus to be able to provide adjustments of the engine adapted to all the possible values of the mixture between 0% and 100% of bio-fuels as a function of the temperature of the product.

OBJECT OF THE INVENTION

The invention aims at remedying such problems by providing a method for optimising the operation of a thermal engine supplied with bio-fuel, wherein said bio-fuel is analysed with accuracy in order to provide adjustments of the engine which are best suited to the fuel.

For this purpose, the invention relates to a method for optimising the operation of a thermal engine the combustion parameters of which are controlled by an electronic housing and at least an engine mapping including:
- a step of carrying out a near-infrared spectroscopic analysis of a bio-fuel containing a mixture of alcohols and/or ethers and/or water in order to determine the proportion of water of at least one other oxygenated compound of the alcohol and/or ether type contained in the biofuel; and
- a step of selecting and/or modifying said mapping on the basis of the result of the analysis in order to optimise the operation of the thermal engine.

Then, according to the invention, the water content in the bio-fuel is determined and taken into account for selecting and/or modifying the engine mapping in order to optimise the operation of the thermal engine.

In addition, knowing the water content makes it possible to determine more accurately the proportions of the other oxygenated compounds such as alcohol and ether contained in the bio-fuel in order to make the best adjustment of the engine.

Such an analysis makes it possible for the electronic or the digital system to adjust at best and in real time the parameters, laws and mapping of injection, of combustion and post-treatment of the engine as a function of the measured results, more particularly the parameters relating to the injection, to the adjustment of the air-fuel mixture and the management of the post-treatment, as well as the validation of the output of the oxygen sensor.

Thus, the invention meets the need for a pertinent and precise determination of the qualitative and quantitative measurement of the bio-fuel and more particularly the need for carrying out a step of analysis of the percentage of the oxygenated component thereof, composed of an alcohol-water and/or ether mixture and a base fuel as a function of the type and quantity of alcohol and/or ethers and/or water and on a type of the basic fuel and a correction of said analysis as a function of the temperature of the bio-fuel, and a step of selecting or modifying said mapping as a function of the result of said analysis.

The method according to the invention meets the problems consisting in directly measuring in the bio-fuel the oxygen content and more precisely in determining the content and type of alcohols, the water content, the ether compound content such as MTBE and ETBE in the gasoline and diesel bio-fuels while taking into account and correcting the various effects of the molecular interactions and the effect of temperature.

Starting from such information, it is possible to correct and to predict the physico-chemical property of the bio-fuel, more particularly its volumic mass, its combustion indexes such as the engine or research octane index or the cetane index, its distillation curve, its volatility and its vapour pressure or its drivability index or the V/L ratio or its cold characteristics.

Advantageously, the mapping is selected and/or modified in order to optimise the consumption of fuel and limit the exhaust gas emissions at ISO performance of the engine or for increasing the motor performances at ISO consumption and the emissions.

Advantageously, the step of the near-infrared analysis of the bio-fuel includes a phase of correction as a function of the multiple overlappings of characteristic bands associated with bonds of the oxygen atoms present in the bio-fuel and more particularly the R—O—H bonds present in the primary alcohols and/or the C—O—C bonds present in the esters and/or the H—O—H bonds present in the molecule of water.

Advantageously, the step of the near-infrared analysis includes a phase of correction as a function of the interactions on the area of harmonics or combinations resulting from the artefacts of resonances of interactions or of a coupling.

Advantageously, the step of the near-infrared analysis includes a phase of correction as a function of the molecular structure and more particularly the number and type of C—C and C—H bonds from said fuel base generated by the crude oil refining process.

Advantageously, the step of near-infrared analysis includes a phase of correction of said analysis as a function of the measurement of the bio-fuel temperature from at least one temperature detector.

Preferably, the near-infrared analysis of the composition of the bio-fuel makes it possible to carry out a phase of correction of the predictions of the physico-chemical properties of said bio-fuel.

Advantageously, the spectroscopic near-infrared analysis is carried out by a sensor carrying out measurements in the spectrum regions between 780 nm and 2,500 nm, preferably in the silicon detection zones between 850 and 980 nm.

Other objects and advantages of the invention will appear during the following description which is made while referring to the appended drawings.

BRIEF DESCRIPTION OF THE FIGURES

FIG. 1 shows the very good spectral repeatability of a near-infrared spectrum measured in intensity in the 850-980 nm region of a fuel of the gasoline type characterised by a research octane index of 80 points.

FIG. 2 shows the variability and a non-linear effect of the variation in the research octane number of fuels of the gasoline type between 75 points and 105 points of octane on the near-infrared spectrum measured in intensity in the 850-980 nm region.

FIG. 3 shows the impact on the non-linear effect of temperature on the near-infrared spectrum in intensity measured in the 850-980 nm region of a fuel between −45° and +50° C.

FIG. 4 shows the impact of the non-linear effect of adding anhydrous ethanol into a product having a research octane of 80 points between 0% and 100% of the near-infrared spectrum in intensity measured in the 850-980 nm region.

FIG. 5 shows the impact of the non-linear effect of adding water into the 7% and 10% anhydrous ethanol on the near-infrared spectrum in intensity measured in the 850-980 nm region.

FIG. 6 shows the impact of the non-linear effect of the simultaneous addition of water and ethanol into one fuel of the gasoline type characterised by a research octane number of 85 points on a near-infrared spectrum in intensity measured in the 850-980 nm region.

FIG. 7 shows the non-linear impact of the addition of ETBE ester on the near-infrared spectrum in intensity measured in the 850-980 nm region of the fuel of the gasoline type having a research octane number of 93.

FIG. 8 shows the non-linear impact of adding ethanol in percent by volume on the research octane number and the engine octane number of a fuel of the gasoline type.

FIG. 9 shows the azeotrope resulting from the addition of 10% by volume of ethanol, 10% by volume of methanol and 7% by volume of MTBE on the distillation curve in degrees Celsius according to the ASTM D86 method on an oil product of the gasoline type.

FIG. 10 shows the non-linear impact of adding of ethanol in percent by volume on the vapour pressure of an oil product in KPa.

FIG. 11 shows the variability according to the origin of the oxygenated compound and the non-linear impact of adding MTBE, ethanol and methanol on the measurement Reid vapour pressure in PSI.

FIG. 12 shows the impact of the starting value of the Reid vapour pressure in PSI of the fuel on the gain in the final vapour pressure of the fuel-ethanol or fuel-methanol mixture at 10% by volume.

EXAMPLARY EMBODIMENT

Figure 1:
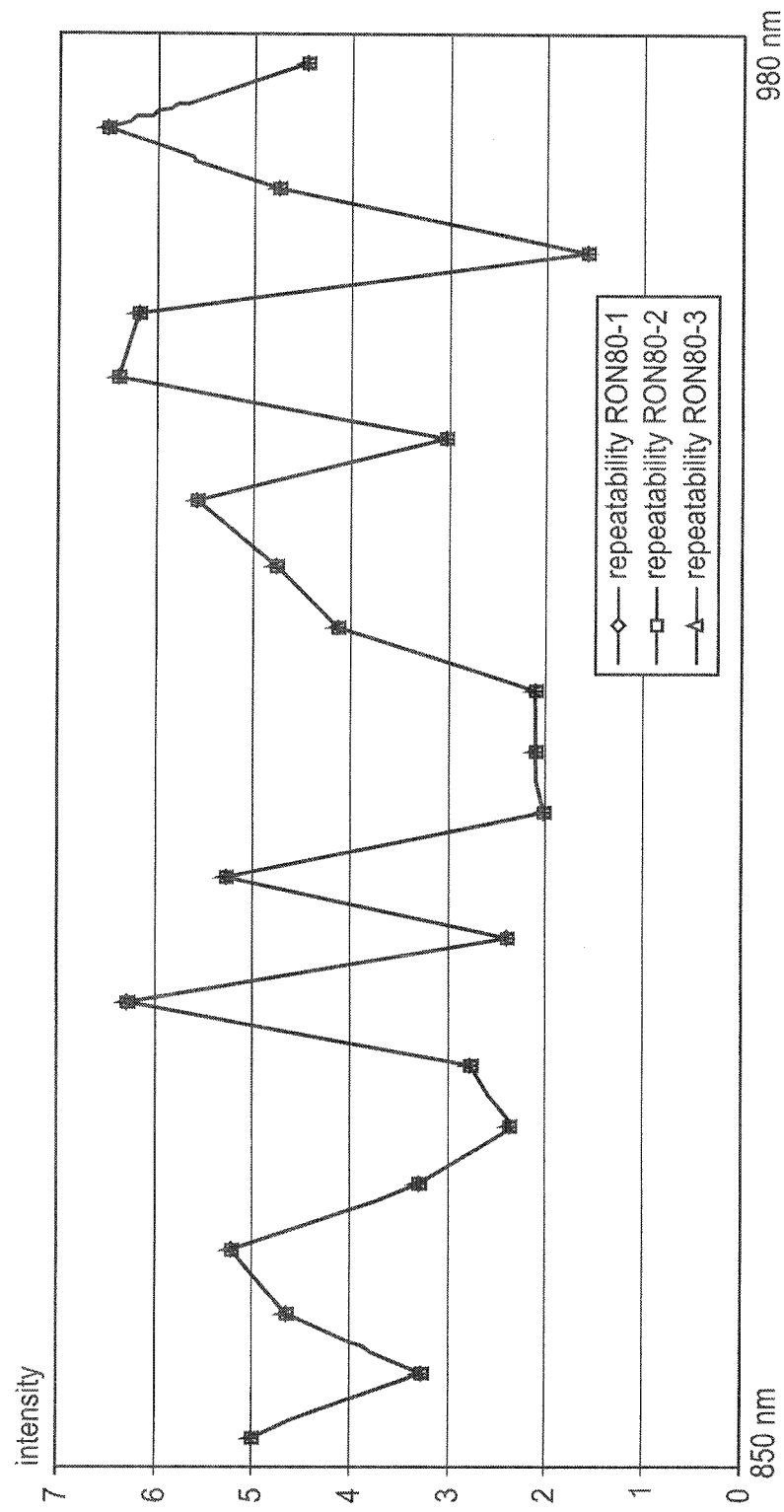
FIGS. 1 to 7 show the various non-linear effects on the intensity of the spectral measurement according to the configured wavelengths in the 850-980 nm region through the combined or not combined addition of oxygenated compounds of the ether and/or water and/or alcohol type and/or temperature.

The invention relates to a method for optimising a thermal engine the parameters, laws and mapping of injection, combustion and post-treatment of which are controlled by an electronic or digital system.

During the method, a step of analysis and of recognition of the oxygenated compound contents is carried out more particularly of the structures and the functions of the water and alcohol and/or ether type of the bio-fuel which are relevant for the fuel-engine couple.

The analysis is carried out from at least one sensor positioned in the fuel circuit of the engine which includes the filling system, the tank, the pumps, the fuel filters, the engine supply circuit and the return circuit to the tank.

The method further comprises a step of selecting or modifying parameters, laws or mappings as a function of the result of said analysis.

According to one embodiment, the step of the relevant analysis of the bio-fuel includes a step of measuring the temperature of a product from at least one temperature sensor of the thermocouple type and a step of spectroscopic analysis of the molecular structure of the hydrocarbons composing the fuel for recognising the carbon-oxygen or carbon-hydrogen molecular bonds as a function of their initial chemical groups more particularly of the alcohol and/or water and/or ethers types and their respective quantification in percentage by mass or percentage by volume as a function of the temperature of the mixture and the intramolecular interactions.

As a matter of fact, even though it is desirable and possible to stabilise the temperature of the bio-fuel during the spectroscopic analysis in a limited range of temperature, it is necessary to check and thus to measure such temperature in order to correct the results of the analysis, if need be.

According to one particular embodiment, the spectroscopic analysis consists of a near-infrared analysis of the fuel. The near-infrared is particularly well suitable for the analysis of the molecular structure since it is an extremely sensitive method, since the near-infrared spectrum can be considered as the product DNA. The molecular structure extracted from such spectrum is very rich for the motor control. In addition, the near-infrared is particularly repeatable. It is well-known that the prediction through the near-infrared type spectroscopic method requires beforehand the constitution of a sufficiently relevant calibration database making it possible to determine the best models and the correlation regions between the various functions and R—OH (primary alcohol), C—O—C (ether), H—O—H (water) groups, the near-infrared spectrum as a function of the temperature. The database must mention the elements which are or not related to the components, the percentage in the mixture thereof, the near-infrared spectrum thereof, the temperature of the sample at the time of the measurement and to all the physical chemical data of the mixtures or the pure products, the computation in percent by volume, in percent by weight or any other possible weightings such as energy, enthalpy or lengths of atomic bonds of the number of carbon, hydrogen and oxygen atoms or C—H, C—O, O—H bonds in absolute value or in ratio of the ones to the others.

In the embodiment with or without stabilisation of the temperature upon the measurement of the near-infrared spectrum, the protocol of preparation of the database thus makes it possible to determine the oxygen content relating to the integration of alcohol of the primary type, water and esters of the ETBE and MTBE types is as follows:

A step of selecting approximately twenty current not oxygenated fuels or fuel bases which are noted $C_{(i)}$ (i varying from 1 to n) from the whole world or proto-fuels, covering an engine octane variation range from RON75 to RON105 and a vapour pressure range from 25 to 100 KPa and various levels of the C/H ratio and the C—C bond of the sigma or pi type.

The near-infrared spectrum in absorbance or in intensity of such products noted $S_{C(i, t)}$ are measured from a definite order through the random selection on a range of temperature t which can go from −50° C. to 150° C.

Then, a random selection is carried out to define the order and the preparation of the alcohol mixtures noted $A_{(j)}$ (j varying from 1 to m), preferably primary alcohols having 1 to 4 atoms of carbon. The mixtures can use 1, 2, 3 or 4 alcohols simultaneously with minimum ratios of 5% in the mixture, preferably 20%. The base favours the number of samples using ethanol. Then, the near-infrared spectrum of the alcohols noted $S_{A(j)}$ is then measured.

A third step is then carried out which consists of a random selection to define the order of the preparation of the ethers ETEB and MTBE mixtures noted $E_{(k)}$ (k varying from 1 to p). Then, the near-infrared spectrum of the ethers noted $S_{E(k)}$ is measured.

Then, in a fourth step the bio-fuels noted $M_{(i,j,k)}$ are prepared executing a random selection in order to define the order from a certain quantity of bases $C_i$ and alcohols $A_j$ and ethers $E_{(k)}$. The final quantity of alcohol makes it possible to cover the range from 0 to 100% (E0 to E100) and the quantity of ethers from 0% to 50%.

The spectrum of bio-fuels $M_{(i,j,k)}$ is measured by carrying out a random selection to define the order by varying the temperature t of the sample on the whole range of temperatures defined to obtain the spectra in absorbance or in intensity $S_{M(i,j,k,t)}$.

In the fourth step, a random selection is carried out to define the order of the addition of water into bio-fuels of a second level noted $MO_{(i,j,k,t)}$ carried out during the preceding step with the percentages varying as a function of the alcohol content of the mixture and as a function of the temperature of bio-fuels on a range defined in order to avoid unmixing phenomena. The percentage of water in the final mixture may vary from 0% to 10%. Then, the near-infrared spectra in absorbance or in intensity are also measured on the same range of variation of temperature $S_{MO(i,j,k,t)}$.

All samples are prepared at least 3 times and the near-infrared spectra of the samples are measured 20 times over a period of 3 weeks. The products are packed in a cold room or in freezers in order to avoid any evaporation. The physical chemical analysis of the products C, A, M and MO are also measured 3 times on 3 different samples.

Figure 2:
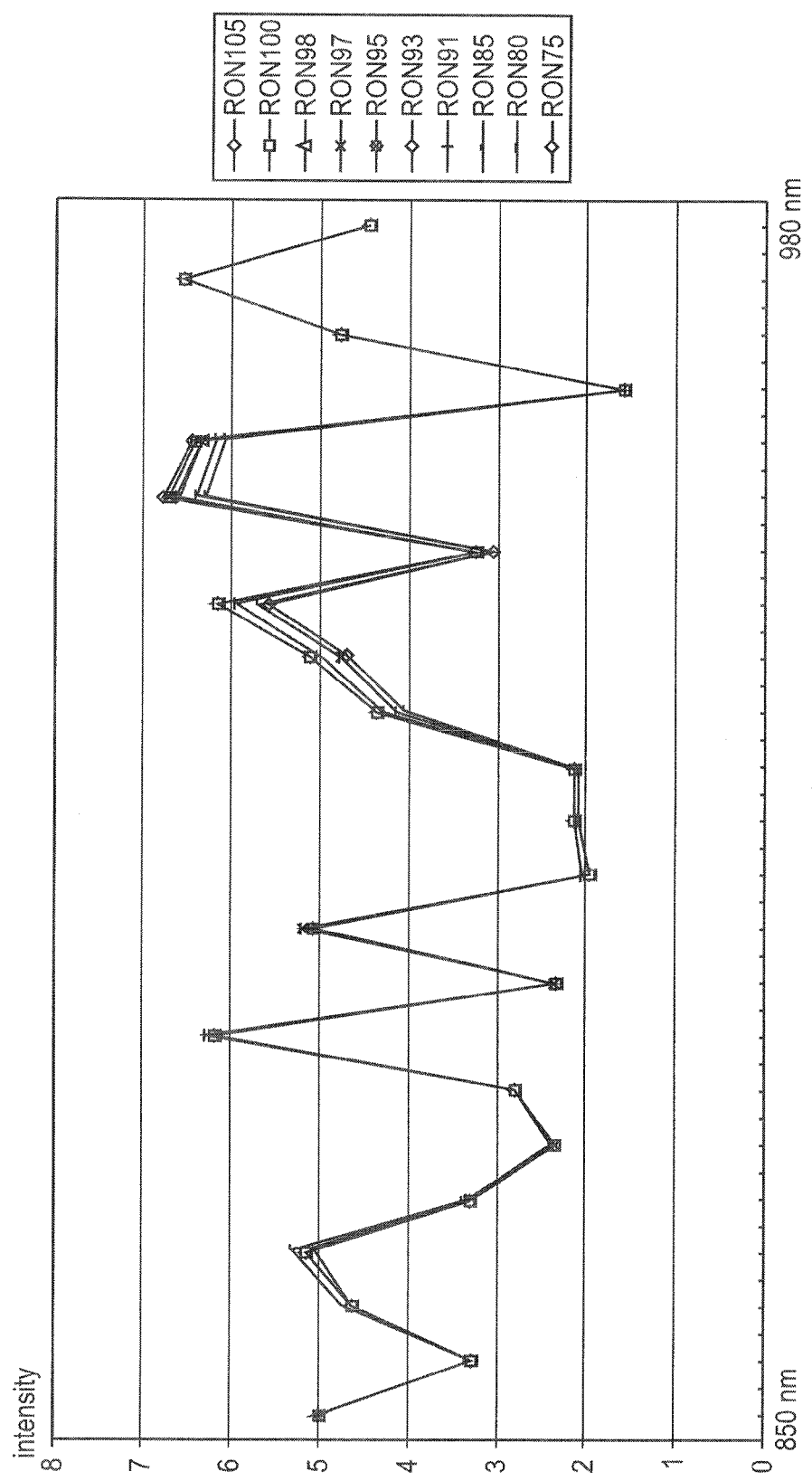
Figure 3:
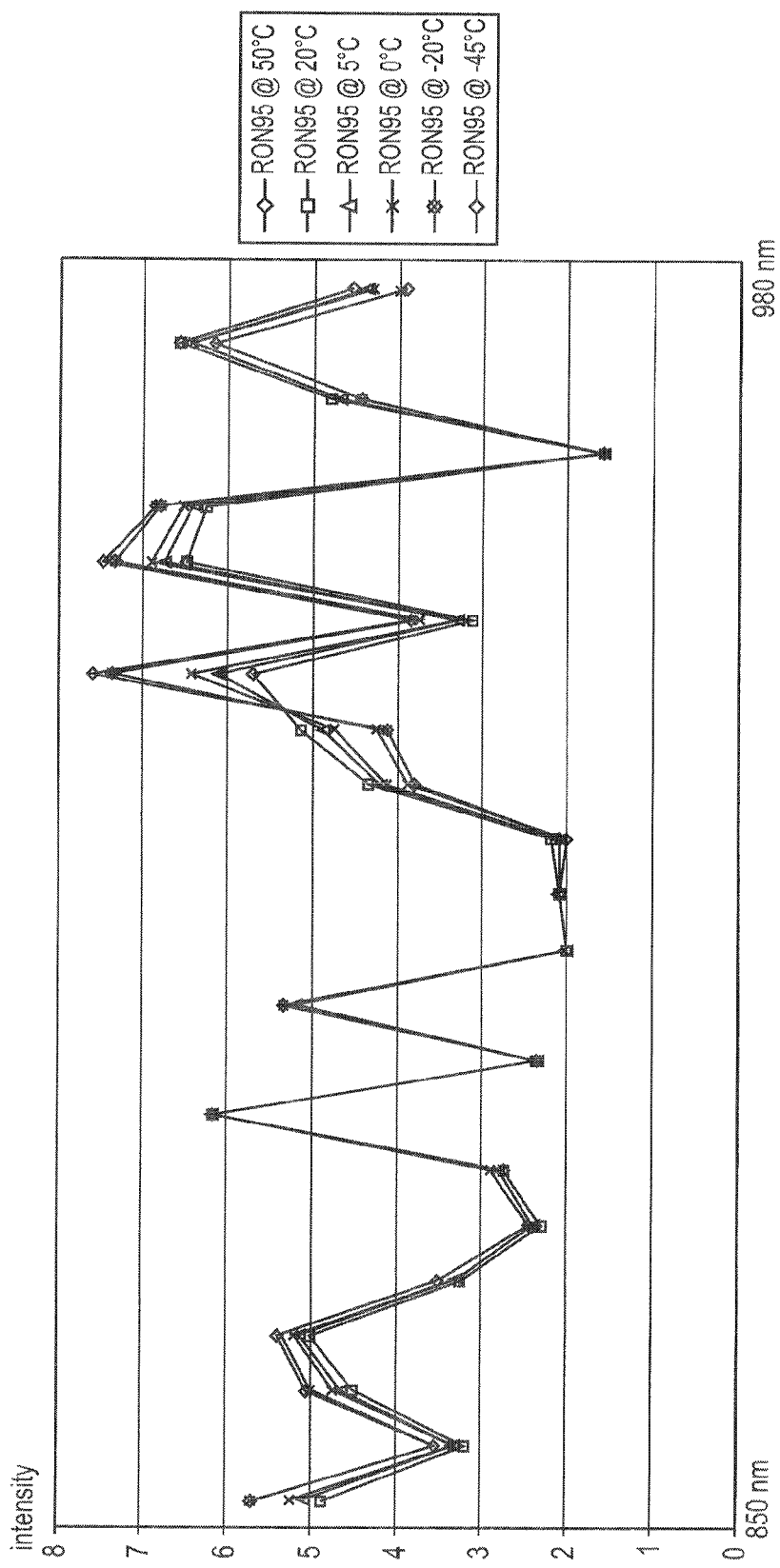
Figure 4:
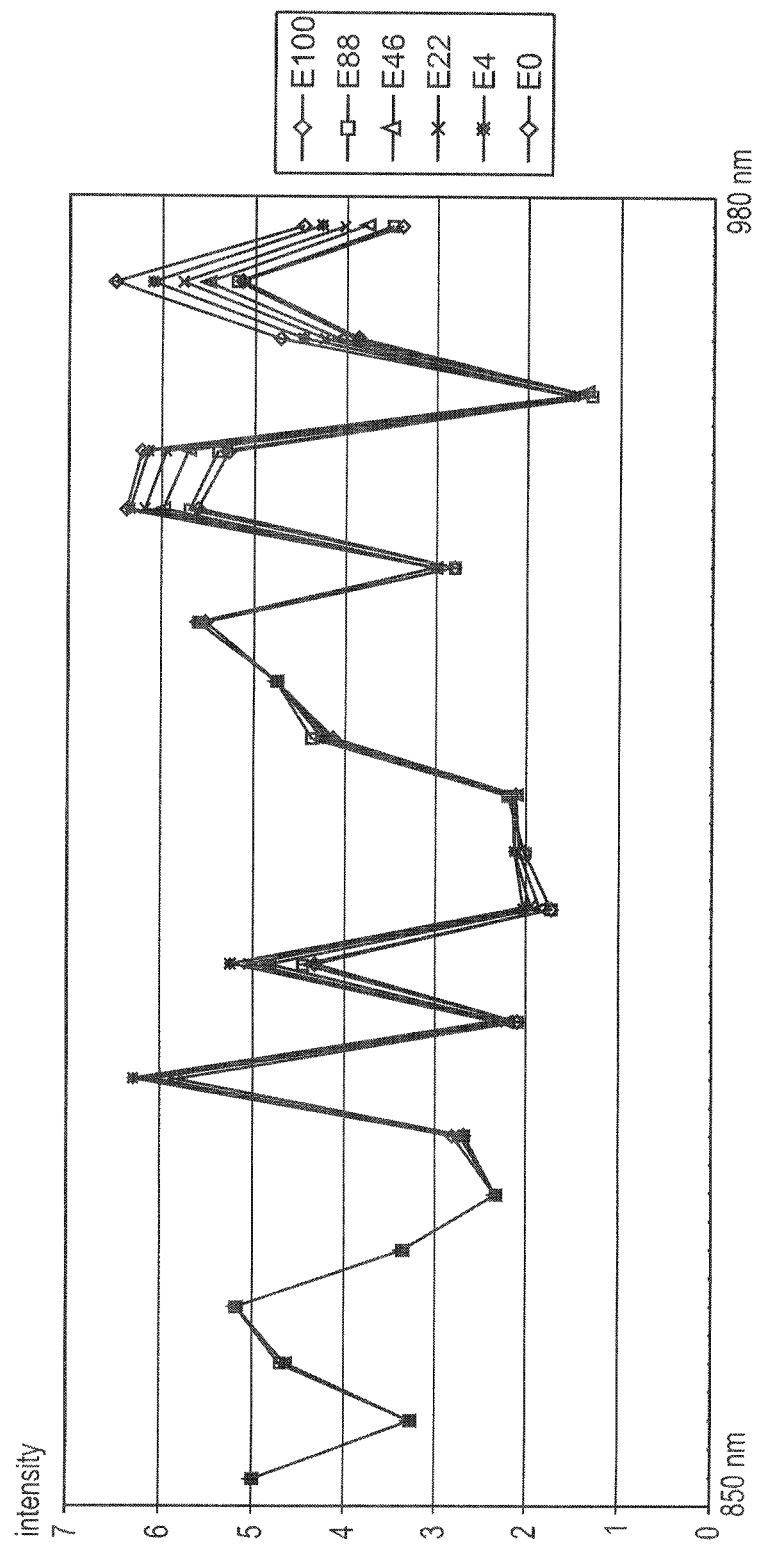
Figure 5:
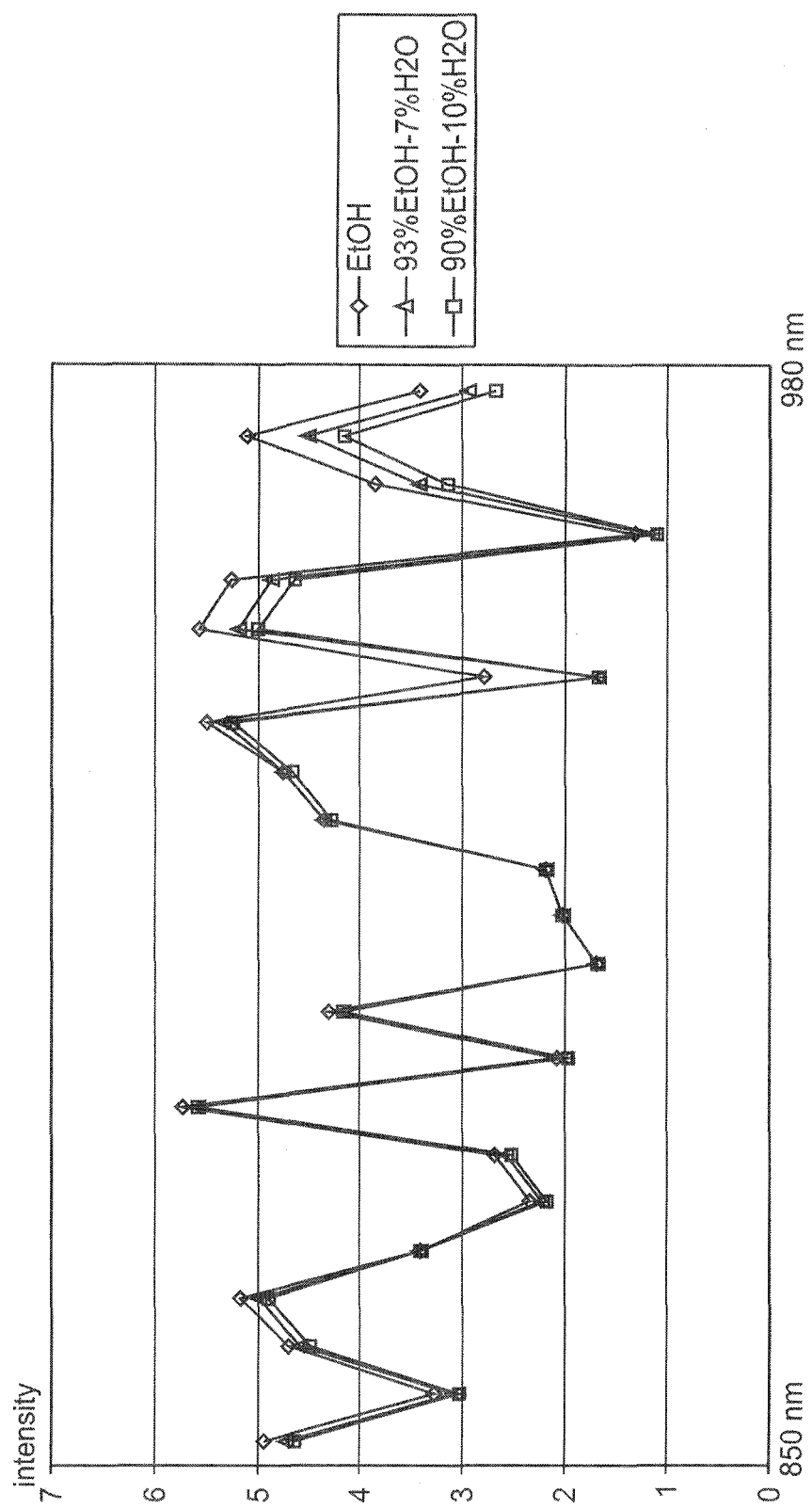
Figure 6:
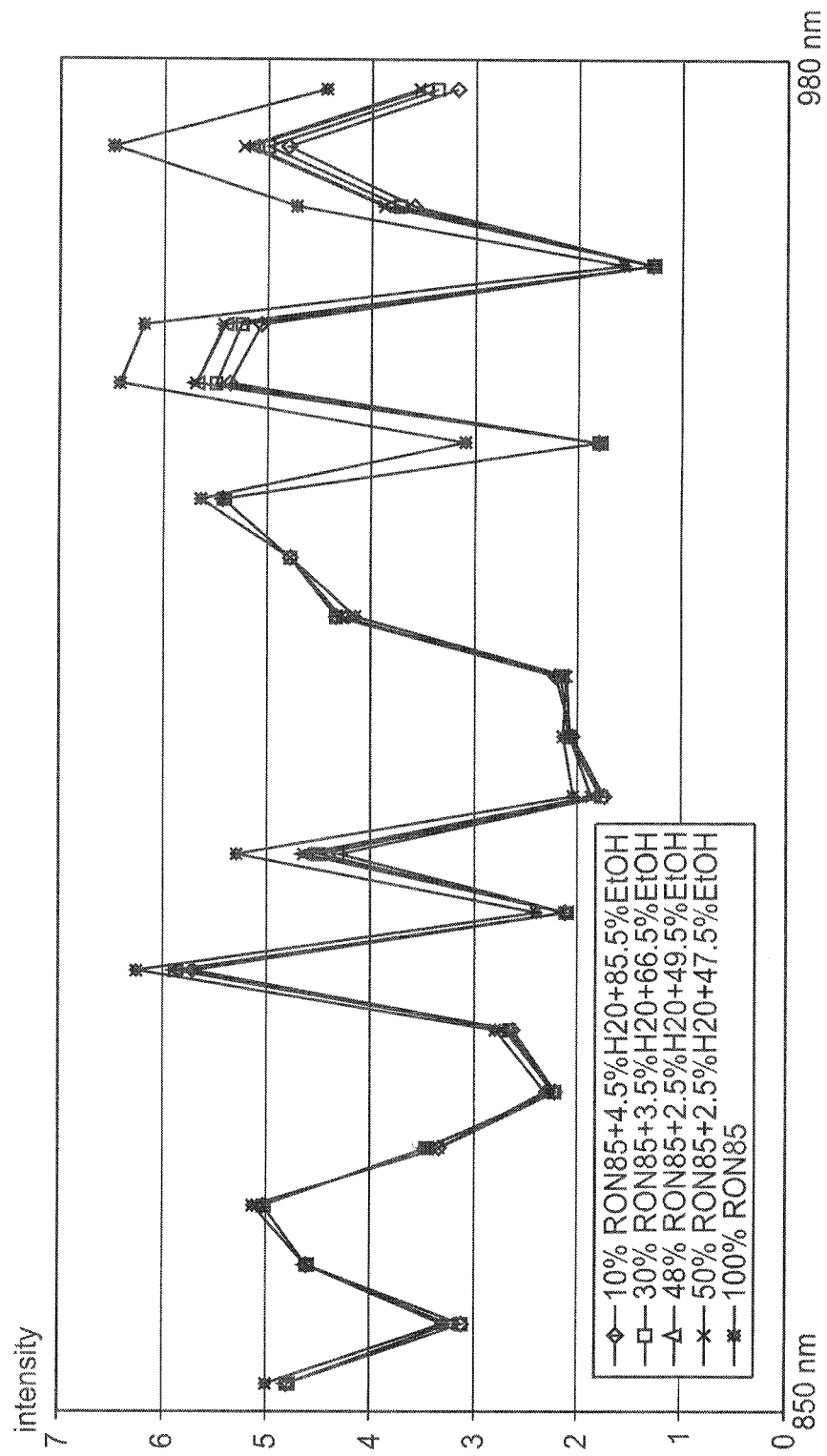
Figure 7:
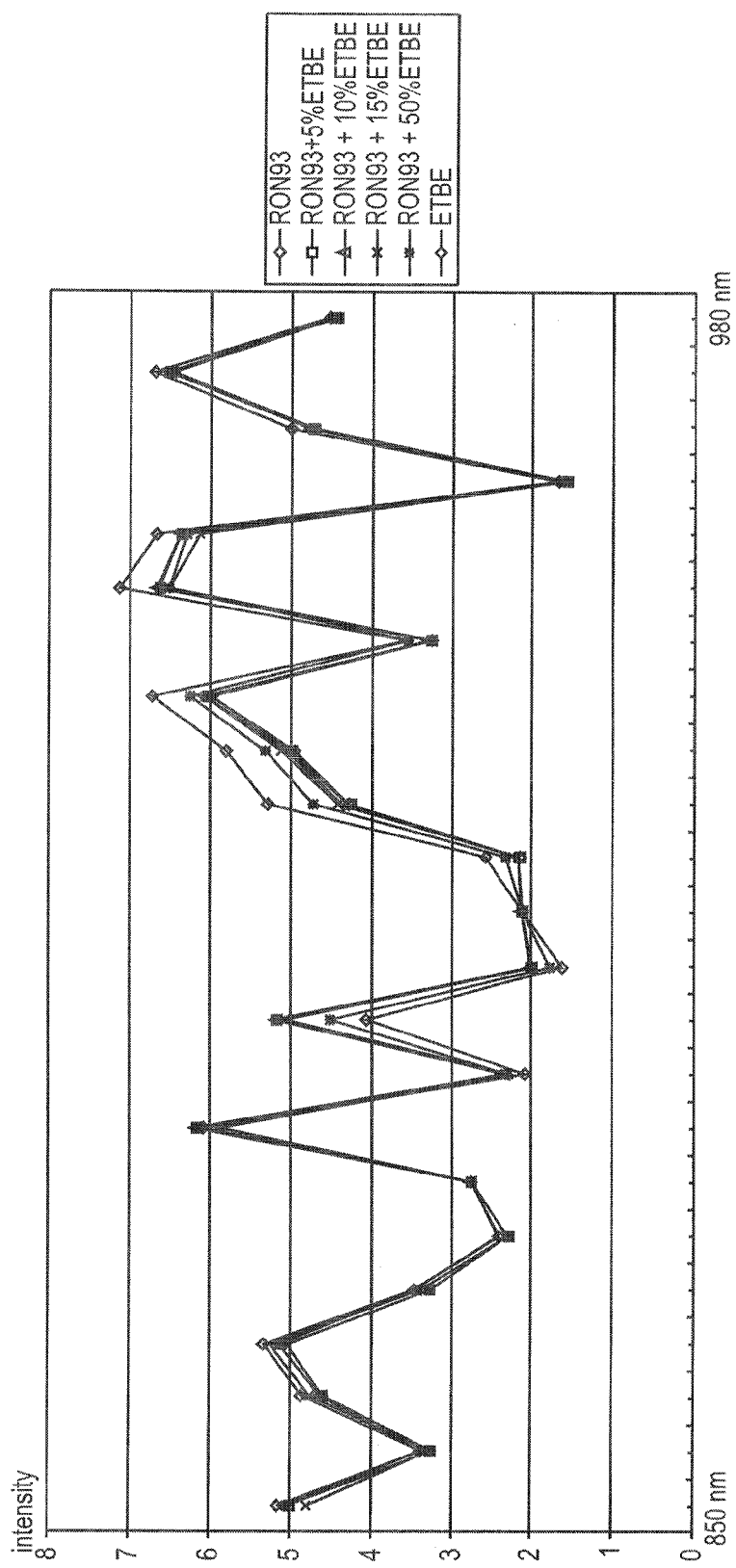
Figure 8:
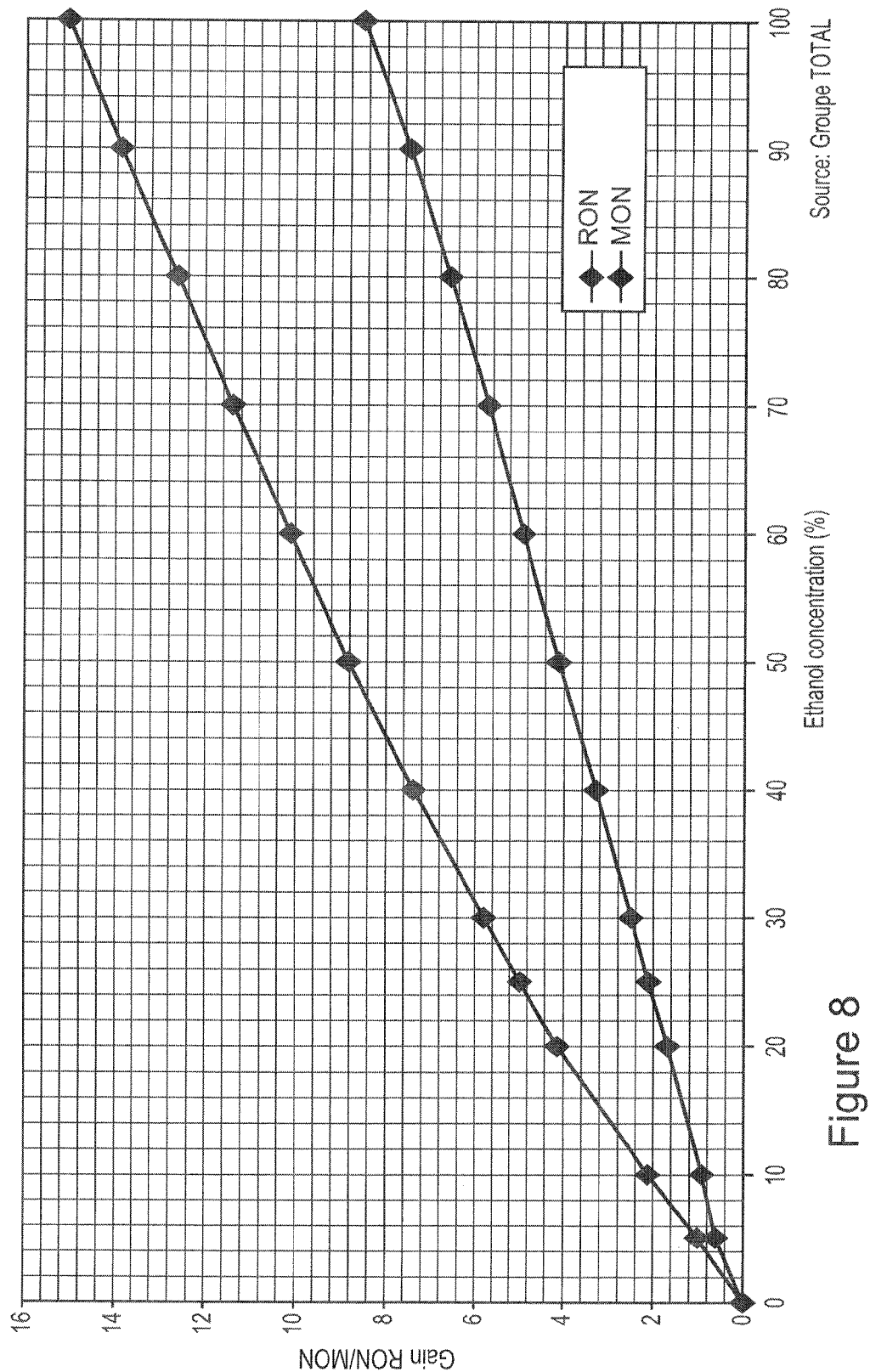
FIGS. 8 to 12 show the non-linear impact and the cross interactions of adding oxygenated products on the physical chemical properties of fuels such as octane numbers, distillation curve and the vapour pressure; these are determining properties in the optimisation of cold engine start and warm engine start of vehicles as well as in the optimisation of the combustion, engine knock limit and in the post-treatment.
Figure 9:
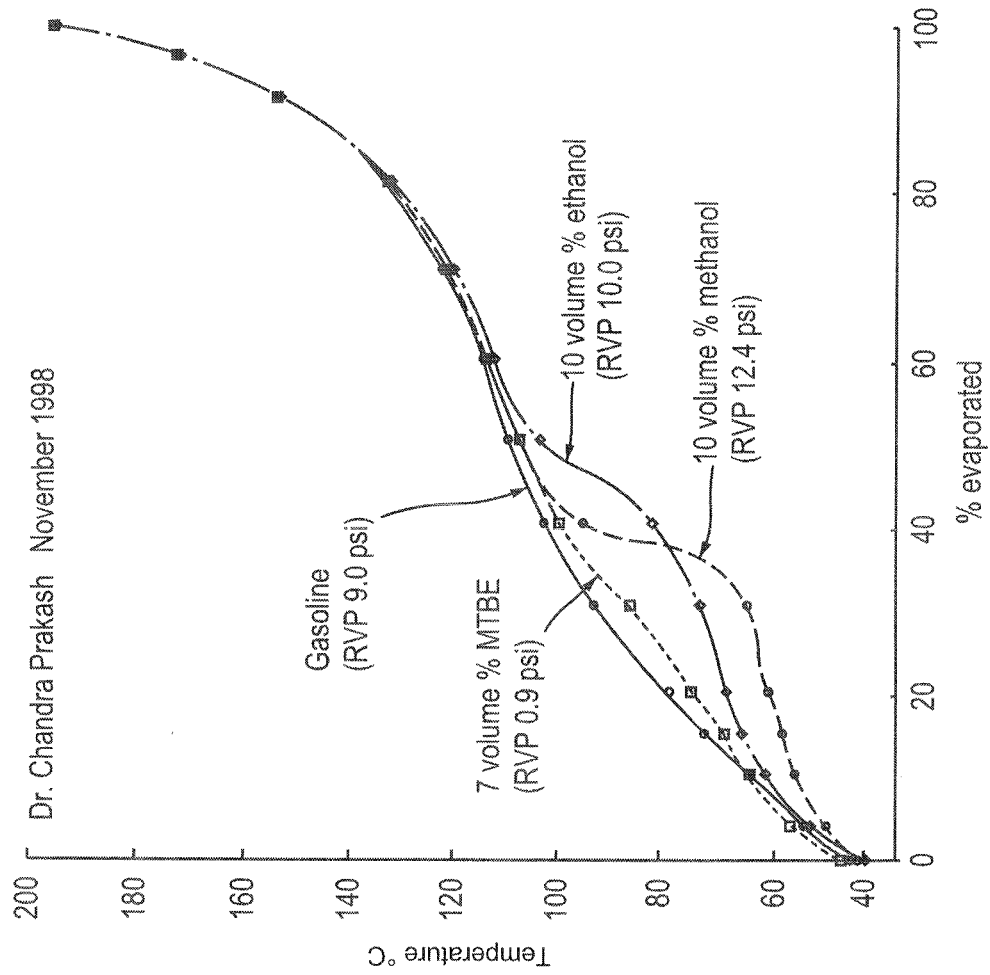
Figure 10:
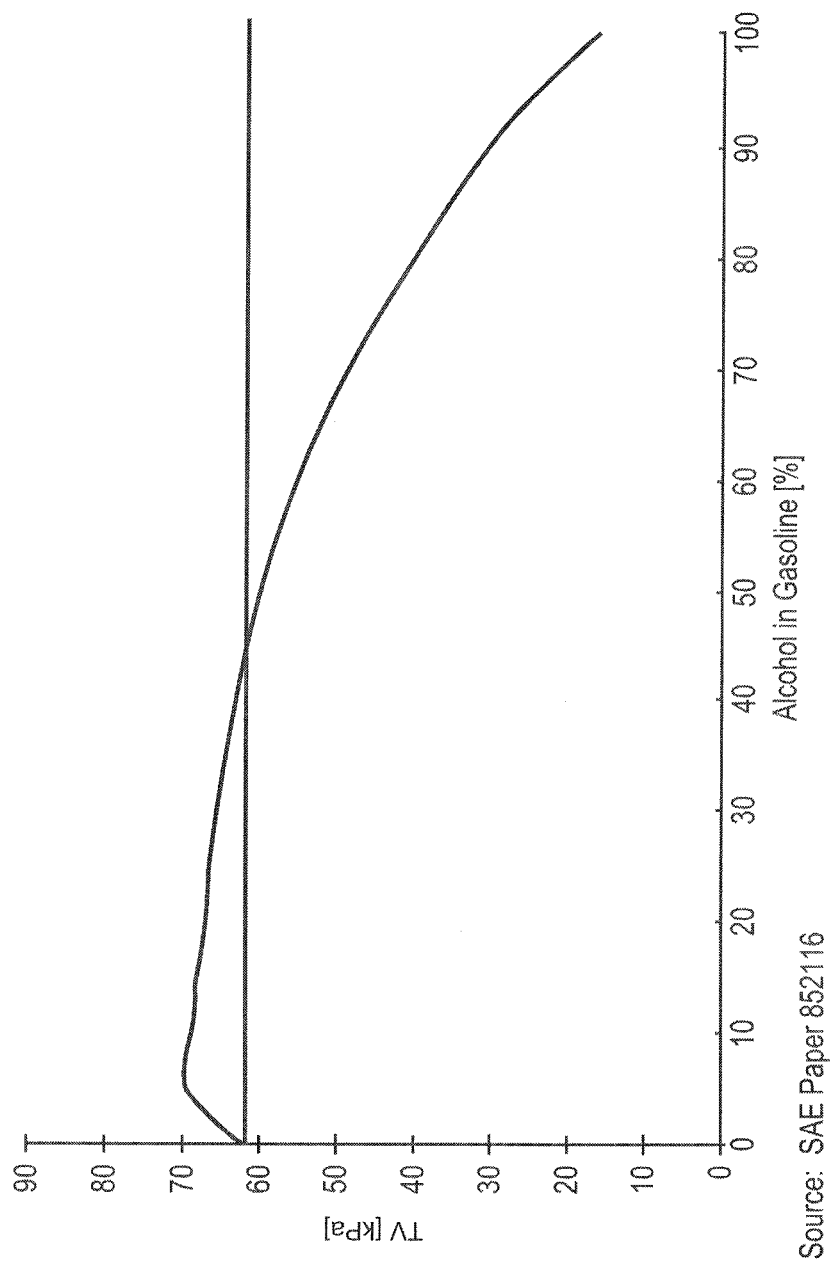
Figure 11:
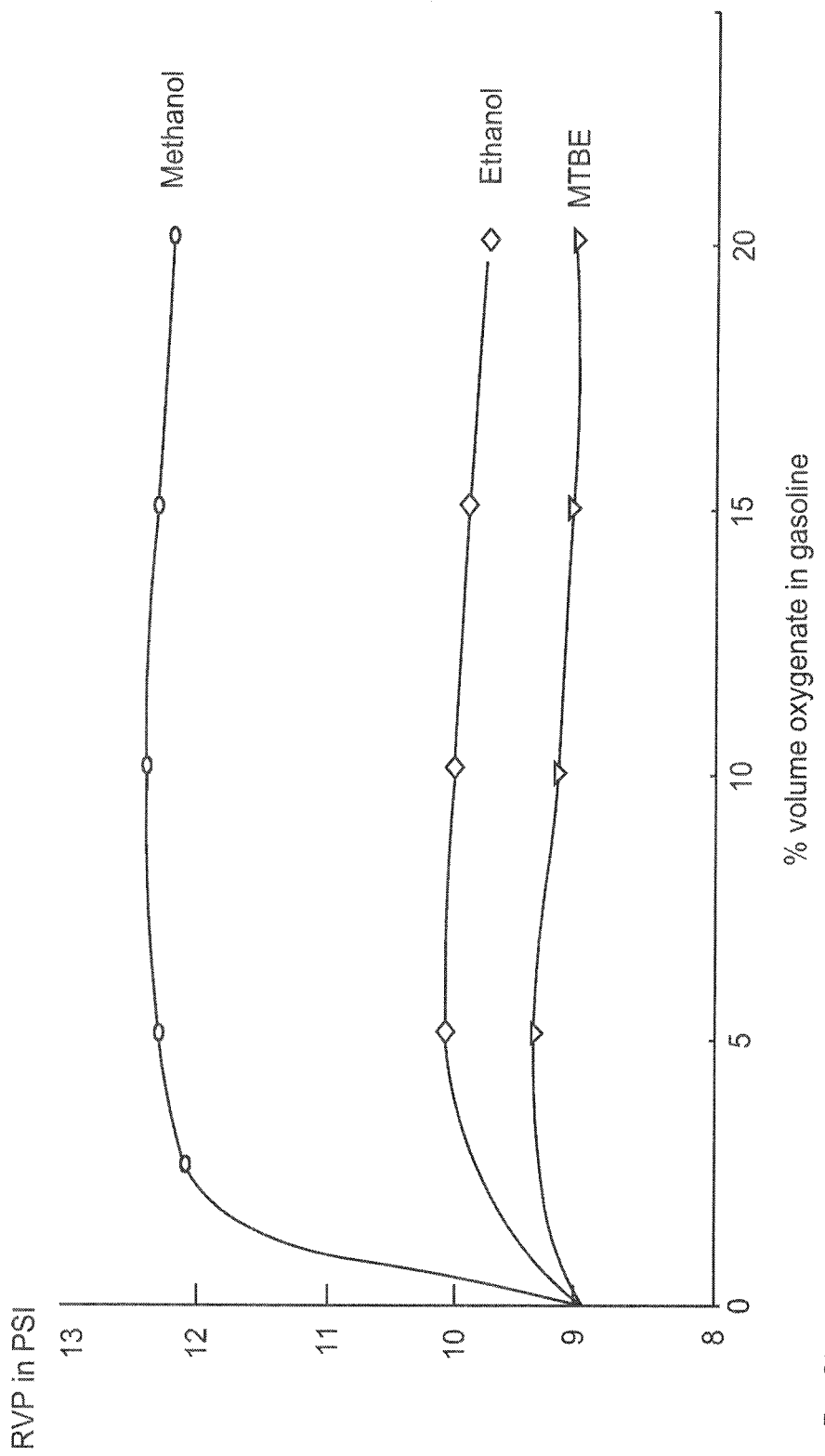
Figure 12:
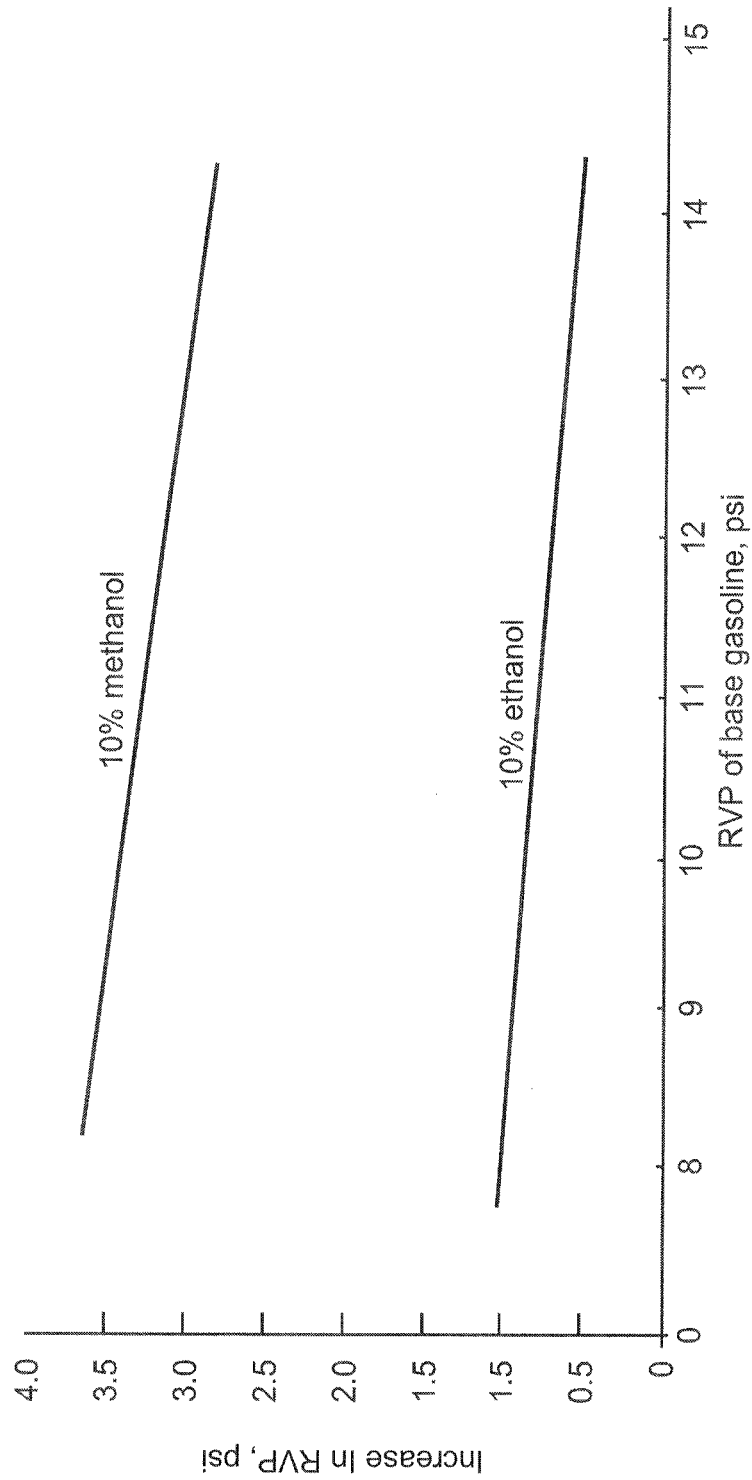
Figure 13:
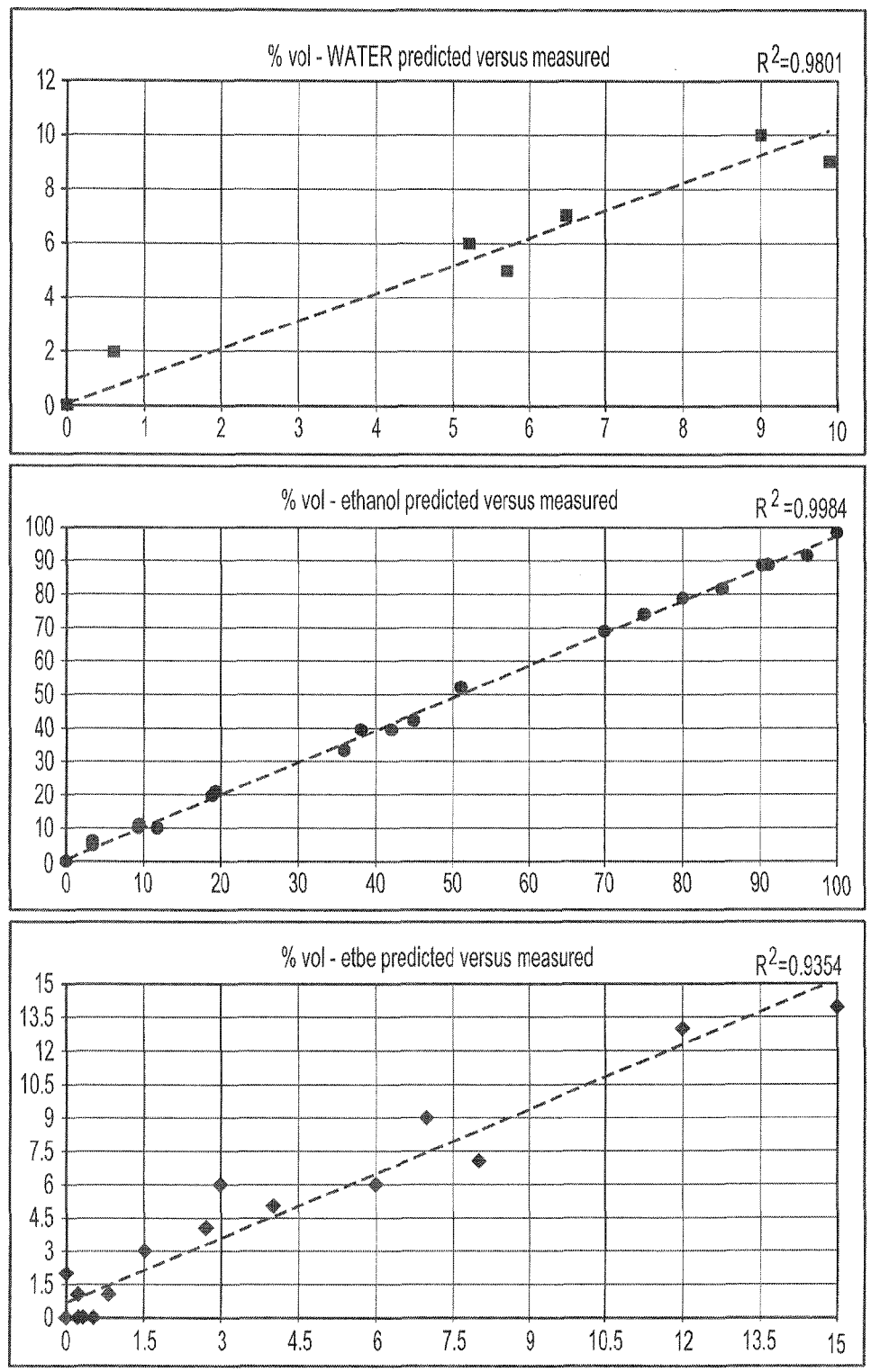
FIG. 13 shows diagrams of the results of the predictive models on the samples which do not belong to the databases on the percentages computed with respect to the real data on water, ethanol and ETBE.

As shown in FIGS. 1 to 7, the interactions and the effects are combined and/or superimposed on the whole spectrum and consequently it is necessary to be able to extract each considered effect independently from the others. Therefore, the more relevant wavelengths regions must be mathematically determined according to an order of priority as a function of the correlation thereof with:
  no effect, the wavelength or wavelengths or the best combination of wavelengths which have unvarying values of intensity and noted B__0 and which can be considered as a lever point or points or a basic line
  one and only one effect such as [temperature], [type of alcohol], [% of (H—O—H bond)], [% of (R—O—H bond)], [% of (C—O—C bond)]
  2 by 2 effects, for example [T°, % of (H—O—H bond)], [% of (H—O—H bond)], [% of (R—O—H bond)], [% of (R—O—H bond), % of (C—O—C bond)], [% of (C—O—C bond), fuel base type], [fuel base type, T° ]
  3 by 3 effects, for example [% of (H—O—H bond, % of (R—O—H bond, alcohol type], [T°, fuel base type, % of (O—O—C bond)].

Then, during the step of constitution of the database, it is possible to use methods based on experimental designs and mixtures of designs in order to reduce the size of the database and the number of measurements to be carried out and to directly and mainly measure the impact of the main interactions of the first and second orders. The multi-coefficient methods of the factorial analysis discriminating as regards the component can also be used. The main advice is to apply standard knowledge models based on theory, document watch and strictly validated by an experiment.

From a well-built database, it is possible to extract the most significant correlations between the intensities and absorbance of the spectrum as a function of the wavelengths and temperature and parameters such as water content, alcohol content, type of alcohol, esters content. Correlation models may be linear or non-linear.

In one particular embodiment, a method of calculation is described for determining the various values searched in the silicon detection region between [780-1, 100 nm] and more precisely [850-980 nm].

In a first step, the total content of oxygenated compounds in the mixture noted P_Ox is measured. It is possible to apply a mathematical correction of the value as a function of the product temperature. The measurement of oxygenated compounds is carried out about the measurement of the spectral intensity or the value of the maximum absorbance between 950 and 980 nm more precisely centred around 970 nm and 962 nm or the best possible combination of the wavelengths in the range of [950-980 nm] playing the part of a weighted smoothing function weighted by the value of the lever point B__0.

In a second step, the value of the water content (H—O—H bond) noted P_H$_2$O is determined while carrying out a measurement of the signal intensity of the values of absorbance between 900 and 910 nm, more precisely centred about the value 905 nm or the best possible combination of wavelengths in the scope of [900-910 nm] playing the part of the smoothing function by applying a mathematical correction of the value as a function of the temperature of the product weighted by the value of the lever point B__0.

In a third step, the content in oxygenated compound of the ether type (C—O—C bond) noted P_ETHER is determined by carrying out a measurement of the intensity of the signal or values of absorbance between 890 and 910 nm, more precisely centred about the value 900 nm and/or values of absorbance between 910 and 920 nm more precisely centred around the value 915 nm or the best possible combination playing the part of the smoothing of wavelengths within the scope of [890-910 nm] and the scope [910-920 nm] by applying a mathematical correction of the value as a function of the temperature of the product weighted by the value of the lever point B__0.

The order of the 3 steps is not critical and these steps can be carried out in any order.

In this particular mode of calculation where temperature is taken into account in each sub-calculation, the percentage of alcohol noted P_OL is determined using the following equation:

$$P\_OL = r P\_Ox - a P\_H_2O - b P\_ETHER \text{ with } (a,b,r) \text{ being constant}$$

a and b being coefficients for correcting the values of absorbance or spectral intensity proportional respectively to the numbers of H—O—H and C—O—C bonds which interact in the range of P_Ox between [950-980 nm].

r being a correction coefficient of the oxygen content in the mixture with respect to the molecular structure of the gasoline base using the number of bonds of the aromatic, iso-paraffin, paraffin, olefinic, naphthenic type as a function of the spectrum [850 nm-980 nm] and more particularly the range between [900-920 nm] more precisely centred about the value 910 nm or the best possible combination of the wavelengths in the range [900-920 nm] with respect to the value of the lever point B__0.

The various so-called smoothing functions in each one of the areas considered make it possible to minimise the effects of drifts resulting from the FERMI, DARLING DENNISON resonances or CORIOLIS interactions.

Any other calculation modes using the same groups or combination of wavelengths recombined in ratio or using one or several linear or non-linear, probabilistic, topological or neuronal network methods can be considered. The correction of the temperature coefficient may also be used in the final computation of P-OL by describing P_OL as a function of temperature. These calculation methods can use modifications of variables (PLS, PCR) or mathematical functions using limited developments or derivatives of various orders or formulae using trigonometry basis such as Log, Log 10, sinus, cosinus or tangent or associated arc measurements.

The invention is described hereabove as an example. It is well understood that the persons skilled in the art will be able to provide various alternative solutions to the embodiments of the invention without however leaving the scope of the invention.

The invention claimed is:

1. A method for optimising the operation of a thermal engine having combustion parameters controlled by an electronic housing and at least one engine mapping, characterised in that the method comprises:
   a step of carrying out a near-infrared spectroscopic analysis of a bio-fuel containing a mixture of alcohols and/or ethers and/or water in order to determine the proportion of water and of at least one other oxygenated compound of the alcohol and/or ether type contained in the bio-fuel; and
   a step of selecting and/or modifying said mapping on the basis of the result of said step of analysis and determination in order to optimise the operation of the thermal engine;
   wherein the step of carrying out a near-infrared spectroscopic analysis of the bio-fuel includes a phase of correction as a function of the multiple overlapping of characteristic bands associated with bonds of the oxygen atoms present in the bio-fuel, wherein the bonds of the oxygen atoms present in the bio-fuel are R—O—H bonds present in primary alcohols and/or C—O—C bonds present in esters and/or H—O—H bonds present in water; and
   wherein the step of carrying out a near-infrared spectroscopic analysis of the bio-fuel also includes a phase of correction as a function of a measurement of the bio-fuel temperature from at least one temperature detector.

2. An optimising method according to claim 1, characterised in that the mapping is selected and/or modified in order to optimise the consumption of fuel and limit the emissions in the exhaust gas at ISO performance of the engine or to increase the performances of the engine at ISO consumption and emissions.

3. A method according any one of claim 1 or 2, characterised in that the step of the near-infrared analysis includes a phase of correction as a function of the interactions on the area of harmonics or combinations resulting from the artifacts of resonances of interactions or of a coupling.

4. A method according to any one of claim 1 or 2, characterised in that the step of the near-infrared analysis includes a phase of correction as a function of the molecular structure and more particularly the number and type of C—C and C—H bonds from said fuel base generated by the crude oil refining process.

5. A method according to claim 1, characterised in that the near-infrared analysis of the composition of the bio-fuel makes it possible to carry out a phase of correction of the predictions of the physico-chemical properties of said bio-fuel.

6. A method according to one of claim 1 or 2, characterised in that the near-infrared spectroscopic analysis is carried out by a sensor executing measurements in the spectrum regions between 780 nm and 2,500 nm.

7. A method according to one of claim 1 or 2, characterised in that the near-infrared spectroscopic analysis is carried out by a sensor executing measurements in the spectrum regions, in the silicon detection zone between 850 and 980 nm.

* * * * *